United States Patent
Draxinger et al.

(10) Patent No.: US 7,794,388 B2
(45) Date of Patent: Sep. 14, 2010

(54) METHOD AND APPARATUS FOR GENERATING AT LEAST ONE SECTION OF A VIRTUAL 3D MODEL OF A BODY INTERIOR

(75) Inventors: Wolfgang Draxinger, Munich (DE); Margarita Noll, Wessling (DE); Herbert Stepp, Planegg (DE); Klaus M. Irion, Emmingen-Liptingen (DE)

(73) Assignees: Karl Storz GmbH & Co. KG (DE); Ludwig-Maximilian-Universitaet (DE)

( * ) Notice: Subject to any disclaimer, the term of this patent is extended or adjusted under 35 U.S.C. 154(b) by 1069 days.

(21) Appl. No.: 11/503,196

(22) Filed: Aug. 11, 2006

(65) Prior Publication Data

US 2007/0060792 A1 Mar. 15, 2007

Related U.S. Application Data

(63) Continuation of application No. PCT/EP2005/001316, filed on Feb. 10, 2005.

(30) Foreign Application Priority Data

Feb. 11, 2004 (DE) .................. 10 2004 008 164

(51) Int. Cl.
*A61B 1/00* (2006.01)
(52) U.S. Cl. ................... 600/101; 600/117; 600/118; 600/108
(58) Field of Classification Search .............. 600/118, 600/108, 117, 109, 101, 407, 411, 424, 476
See application file for complete search history.

(56) References Cited

U.S. PATENT DOCUMENTS 4,986,262 A 1/1991 Saito ............................ 128/6

(Continued)

FOREIGN PATENT DOCUMENTS

DE 195 11 978 A1 10/1996

(Continued)

OTHER PUBLICATIONS

International Preliminary Report on Patentability, May 16, 2006, 8 pages.

(Continued)

*Primary Examiner*—John P Leubecker
(74) *Attorney, Agent, or Firm*—St. Onge Steward Johnston & Reens LLC

(57) ABSTRACT

A method for generating at least one section of a virtual 3D model of a body interior, in particular a hollow organ, uses data that are provided by at least one endoscope introduced into the body interior. The data comprise at least one position and orientation of the endoscope, the at least one position and orientation being assigned at least one distance between the endoscope and the at least one point on a surface of the body interior, and at least one endoscopic image of the surface of the body interior in the region of the at least one point on the surface of the body interior. From the said data relating to a number of different positions and orientations of the endoscope is/are generated the section or sections of the 3D model in superposition with the associated endoscopic image. An appropriate apparatus is also described.

25 Claims, 4 Drawing Sheets

U.S. PATENT DOCUMENTS

| | | | | |
|---|---|---|---|---|
| 5,090,400 A | * | 2/1992 | Saito | 600/108 |
| 5,638,819 A | * | 6/1997 | Manwaring et al. | 600/424 |
| 5,704,897 A | | 1/1998 | Truppe | 600/117 |
| 6,459,481 B1 | * | 10/2002 | Schaack | 356/241.1 |
| 7,232,409 B2 | * | 6/2007 | Hale et al. | 600/118 |
| 2001/0027272 A1 | * | 10/2001 | Saito et al. | 600/426 |
| 2003/0164952 A1 | | 9/2003 | Deichmann et al. | 356/603 |
| 2004/0054248 A1 | * | 3/2004 | Kimchy et al. | 600/3 |
| 2005/0058326 A1 | * | 3/2005 | Barth et al. | 382/128 |
| 2005/0085718 A1 | * | 4/2005 | Shahidi | 600/424 |
| 2005/0203394 A1 | * | 9/2005 | Hauck | 600/437 |
| 2007/0225553 A1 | * | 9/2007 | Shahidi | 600/103 |
| 2007/0236514 A1 | * | 10/2007 | Agusanto et al. | 345/646 |
| 2007/0238981 A1 | * | 10/2007 | Zhu et al. | 600/424 |

FOREIGN PATENT DOCUMENTS

| | | |
|---|---|---|
| DE | 197 50 698 A1 | 5/1998 |
| DE | 297 23 333 U1 | 7/1998 |
| DE | 198 00 765 A1 | 4/1999 |
| DE | 101 04 483 A1 | 10/2002 |
| WO | WO 01/35849 A1 | 5/2001 |

OTHER PUBLICATIONS

International Search Report, May 27, 2005, 3 pages.

* cited by examiner

METHOD AND APPARATUS FOR GENERATING AT LEAST ONE SECTION OF A VIRTUAL 3D MODEL OF A BODY INTERIOR

CROSS-REFERENCE TO RELATED APPLICATIONS

The present application is a continuation of pending International patent application PCT/EP2005/001316 filed on Feb. 10, 2005 which designates the United States and claims priority of German patent application No. 10 2004 008 164.6 filed on Feb. 11, 2004.

BACKGROUND OF THE INVENTION

The invention relates to a method and an apparatus for generating at least one section of a virtual 3D model of a body interior, in particular a hollow organ.

Such a method and such an apparatus are generally applied and/or used in the endoscopic examination of body interiors in the human or animal body. Such a body interior can be, for example, the bladder, the lung, the stomach, the throat, the esophagus, etc.

Without restriction of generality, the present invention is described with reference to the specific application of the examination of the bladder.

In the endoscopic examination of the bladder, the examining doctor attempts to acquire the organ with the endoscope in a fashion covering the area as much as possible, that is to say to "scan" it. It is important in this case that each part of the surface of the bladder is actually acquired or is acquired with adequate care. Whether each part of the surface of the bladder is acquired depends substantially on the experience of the doctor. However, it can occur that regions of the wall of the bladder are overlooked, that is to say are not endoscopically acquired. If the nonacquired regions of the wall of the bladder are, if appropriate, malign tissue areas, this can have serious consequences for the patient.

One reason why omissions of tissue areas or surface areas of the bladder come about during the endoscopic examination of the bladder is that the orientation of the doctor in the substantially spherical interior of the bladder is rendered difficult by the restricted field of view of an endoscope. To be specific, the restricted field of view of an endoscope has the consequence that one and the same endoscopic image cannot acquire the entire surface of the body interior, but only a specific surface area.

Moreover, since the endoscopic image visually displayed on a monitor has no spatial depth but, only a "two-dimensional" effect, it is not possible solely with the aid of the acquired endoscopic image to judge the surface area from which this endoscopic image originates. If, for example, a number of endoscopic images of different surface areas of the body interior are acquired and documented, and if a pathological finding is recorded on one of the endoscopic images, it is no longer possible later on to use the endoscopic images to determine unambiguously from which surface area this endoscopic image with the pathological finding originates.

Thus, it is also difficult for tissue regions treated in previous examinations to be found again in a repeated endoscopic examination, for example when monitoring the course of therapy or conducting tumor aftercare. Here, as well, the doctor is dependent on the quality of the documented findings. Because of the great similarity of the appearance of various surface regions of the inner wall of the bladder on the respective endoscopic image, reliably and quickly refinding a specific surface area of the body interior with adequate reliability is impossible, or possible only conditionally.

There is thus a need to acquire and document images of a body interior in a way that offers improved orientation of the doctor during examination of the body interior and, above all, a possibility for the doctor to establish which surface areas have already been examined and which have not yet been examined. In other words, it is desirable to give the examining doctor a means for navigating the endoscope in the body interior such that he can move the endoscope in the body interior in a targeted fashion so that it is possible for the surface of the body interior to be acquired endoscopically as quickly and completely as possible and documented.

The prior art has already described methods and apparatuses, for example in the document DE 197 50 698 A1, with the aid of which a body interior can be measured in three dimensions in order to generate a virtual model, that is to say a computer model, of the body interior. Described for this purpose in the said document is a plug-on unit for a flexible endoscope into which a probe can be inserted that contains an ordered optical fiber bundle with a cladding. The cladding is provided with equidistant markings that can be acquired with the aid of contactless scanning or readout means. The optical fiber bundle Is assigned an optical imaging means, the optical fiber end being assigned a beam deflecting means that permits the light beam to be deflected at right angles on all sides onto the surface of the measured body interior.

The document U.S. Pat. No. 5,704,897 describes an apparatus and a method that enables an optical display of an endoscopic image to be overlaid with a data field in order to support the navigation of an instrument during endoscopic operations. An endoscopic image is acquired with the aid of an endoscope and displayed on a display screen. Arranged on the endoscope is a position acquisition system the purpose of which is the permanent acquisition of the spatial position of the endoscope. The spatial data field, which forms a model of the body interior, is obtained by means of computed tomography, magnetic resonance tomography or ultrasound, and assigned to a human body in a specific position. A sensor that can be fastened on the patient's body serves the purpose of compensating movements of the body. A computer is used to bring selected points of the data field into agreement with corresponding points of the optical display by displacing specific points of the data field while the latter are superposed on the optical display.

A further document that is concerned with the documentation of courses of treatment is the document DE 297 23 333 U1, which discloses a system for refinding specific locations in a body cavity. This system has a tube for insertion into the body cavity, and an endoscope for optical display of the tissue surfaces surrounding the tube, the tube being at least partially of transparent design and having in its transparent sections optical markings that are aligned reproducibly relative to the patient, such that specific regions of the tissue surface are to be assigned to specific markings, and the specific regions can be refound with the aid of the assignment.

However, all the previously described known methods and apparatuses have the disadvantage that the endoscope is navigated only with the aid of a model specified in advance by an extracorporeal method, but in some circumstances this does not ensure an exact correlation between the respective endoscopy image of a surface area of the body interior and the associated area of the model, and so the disadvantage continues to exist of the risk that specific regions of the body interior can remain out of account during an endoscopic examination.

SUMMARY OF THE INVENTION

It is an object of the invention to provide a method and an apparatus of the type mentioned at the beginning that permits a complete image acquisition of the entire surface of the body interior in a more reliable fashion.

According to the invention, this object is achieved by a method for generating at least one section of a virtual 3D model of a body interior, in particular a hollow organ, from data that are provided by at least one endoscope introduced into the body interior, the data comprising:

at least one position and orientation of the endoscope, the at least one position and orientation being assigned
 at least one distance between the endoscope and at least one point on a surface of the body interior, and
 at least one endoscopic image of the surface of the body interior in the region of the at least one point on the surface of the body interior, the said data relating to a number of different positions and orientations of the endoscope being used to generate the section or sections of the 3D model in superposition with the associated endoscopic image.

With regard to the apparatus mentioned at the beginning, the object is achieved by an apparatus for generating at least one section of a 3D model of a body interior, in particular a hollow organ, comprising at least one endoscope for acquiring at least one endoscopic image of at least one section of a surface of the body interior, a position acquisition system for acquiring the position and orientation of the endoscope, a distance measurement system for acquiring at least one distance of the endoscope in relation to at least one point of the surface of the body interior as a function of the position and orientation of the endoscope, and a data processing system that is designed such that it uses a plurality of points, acquired from different positions and orientations of the endoscope by the distance measurement system, on the surface of the body interior to generate the section or sections of the virtual model of the surface of the body interior, and projects the at least one endoscopic image onto the model thus generated.

Consequently, according to the invention at least one endoscopic image of at least one surface area of the body interior is acquired with at least one endoscope, the position and orientation of the endoscope being acquired in the meantime by means of a position acquisition system. Furthermore, the at least one endoscopic image is processed in a data processing system that includes image processing, the at least one endoscopic image of the at least one surface area In the data processing system being projected onto a corresponding surface area of the virtual model of the body interior. The virtual 3D model of the body interior is obtained by virtue of the fact that a plurality of endoscopic images are acquired from different positions of the endoscope, and in relation to each endoscopic image at least one point is acquired on the surface of the body interior in three dimensions by a distance measurement between the endoscope and the surface of the body interior, preferably in the region of the image field cone on the endoscope, and that the model of the surface of the body interior is generated from the points acquired in three dimensions, and the at least one endoscopic image is projected onto the generated virtual 3D model with the aid of the acquired position and orientation of the endoscope.

In the case of the method and of the apparatus according to the invention, it follows that the virtual 3D model, that is to say the reconstruction of the surface of the body interior as a computer model, is generated simultaneously with the acquisition of a plurality of endoscopic images from different positions of the endoscope. To this end, not only is the endoscope used to acquire endoscopic images, but at the same time the position and orientation of the endoscope Is acquired, for example with reference to a fixed reference point that can be defined, for example, by the insertion hole of the endoscope into the body interior, and moreover the respective distances of the endoscope are acquired in relation to a plurality of points on the surface of the body interior.

From knowledge of the specific endoscope data, specifically viewing direction with reference to the longitudinal axis of the endoscope shaft and numerical aperture of the objective of the endoscope and the data from the position acquisition and distance measurement a virtual model of the surface of the body interior is generated in the data processing system on which the endoscopic images recorded in the case of the position, orientation and distance measurements are superposed. The virtual model is thereby produced in the data processing system at the same time as the texturings of the surface of the tissue of the body interior. In other words, endoscopic images are acquired in one examination operation at the same time as measurements are made for generating the virtual model of the body interior. A multiplicity of coordinates are already obtained during the first endoscopic inspection of the body interior, and they can be used to obtain the complete geometry of the body interior by interpolating between the measured coordinates or extrapolating. In the case of the examination of the bladder, for example, the doctor can directly approach reference points, for example the orifices, and use them as intermediate points for the interpolation. The external urethral opening into the bladder can likewise be used as a further intermediate point, and the corresponding bladder region can be extrapolated therefrom.

The at least one endoscopic image can be linked in real time with the virtual model of the body interior generated with the aid of the method according to the invention and the apparatus according to the invention.

A number of endoscopes that differ from one another with regard to their viewing directions with reference to their longitudinal axis can be used in succession in order to acquire an image of the surface of the body interior; thus, for example, endoscopes having endoscope optics with 0°, 30°, 60°, 90° and 120° optics can be used, or it is possible to use a flexible endoscope whose viewing direction can be varied by deflecting the distal end from the longitudinal axis.

The method according to the invention and the apparatus according to the invention have the advantage, furthermore, that they enable images to be acquired and documented in a fashion very largely independent of displacements and deformations of the body interior, since the virtual model of the body interior can be recorded anew with each examination. Specifically, in the case of examination of a bladder the position and shape of the bladder is a function, inter alia, of the filling of the bladder and of the position of the patient. By permanently measuring the distance between the endoscope and at least one point on the surface of the body interior, such displacements and deformations of the body interior can be found by calculation, thus rendering it possible during each examination to make an informative comparison with the state of the body interior during an earlier examination.

In a preferred refinement of the method, those surface areas of the surface of the body interior of which an endoscopic image has already been acquired are visually marked on the virtual model of the body interior.

The data processing system of the apparatus according to the invention is correspondingly designed such that it marks visually on the virtual model of the body interior those surface areas of which an endoscopic image has already been acquired.

The marking of already inspected surface areas of the body interior on the monitor facilitates the navigation of the endoscope still further for the examining doctor, because he can detect directly from the markings which surface areas have not yet been acquired by an endoscopic image and which he can then approach in a targeted fashion. Moreover, the markings can advantageously be used as an aid to refinding specific surface areas of the body interior for example malign areas, in later examinations, the result being to enable a particularly well targeted reproducible examination of specific surface areas of the body interior.

The marking of the surface areas of the body interior in relation to which an endoscopic image has already been acquired is preferably performed with the aid of the acquisition of the hold time for viewing these areas, with the aid of a different light intensity and/or of a signal that is generated during viewing of a specific area.

In a further preferred refinement of the method, the distance measurement for acquiring in three dimensions the points on the surface of the body interior is performed by means of a contactless distance measurement system that operates in preferred refinements on the basis of at least one laser beam, emitted by the endoscope, on the basis of a triangulation, or by measuring the transit time of the laser beam, on the basis of a pattern projected by the endoscope onto the surface of the body interior, for example a stripe, grid or punctiform pattern, or on the basis of ultrasound, emitted by the endoscope, by measuring the transit time of the ultrasound.

In particular, it is preferably possible to provide that in relation to a position and orientation the distance relating to a number of points on the surface of the body interior that then lie entirely or partially in the field of view of the endoscope is measured.

It is further preferred when the distance measurements and/or position acquisition measurements are carried out in time intervals that are shorter than one second and are preferably in the range of milliseconds or there below, the result being to obtain a particularly exact reproduction of the body interior by means of the virtual model. The distance measurement is preferably automatically triggered in this case by the data processing system or an appropriate control.

The distance measurement system of the apparatus according to the invention is preferably arranged on the endoscope itself, and this has the advantage that the distance measurement system is always permanently correlated with a point or a location on the endoscope.

It is further preferred when the data processing system is designed such that it derives a further virtual 3D model of the body interior from an image of the body interior obtained by an imaging method having a depth effect, for example computed tomography, magnetic resonance, ultrasound.

It is further preferred in this case when the virtual model of the body interior is superposed in the correct position in the data processing system by an image of the body interior obtained by an imaging method having a depth effect, for example computed tomography, magnetic resonance or ultrasound.

This is preferably implemented with regard to the apparatus according to the invention by virtue of the fact that the data processing system is designed such that it superposes on the virtual model of the body interior an image of the body interior stored in the data processing system, for example, and obtained by an imaging method having a depth effect, for example computed tomography, magnetic resonance, ultrasound.

It is advantageous here that at the same as the surface of the body interior is optically acquired it is possible to obtain information relating to the depth of extent of a tumor that has been optically acquired superficially via the associated data from the above named imaging method.

For the purpose of the particularly preferred implementation of a so called look ahead function, it is further preferred when the data processing system is designed so as to enable a viewing mode with the aid of which, starting from the endoscopic image of the surface of the body interior, it is possible to continue to view in the viewing direction of the endoscope the positionally correct 3D information from the imaging 3D method having a depth effect. This provides the examining doctor with the possibility of starting from the endoscopic surface image, to use a "virtual endoscope" to look into the tissue and to examine a malign tissue there even in the extent of its depth, and to evaluate it.

In a further preferred refinement of the method, the model of the surface of the body interior is also derived from endoscopic images that have been obtained at least partially under fluorescence excitation.

The advantage of an improved tumor visualization in the examination of the body interior is achieved with the aid of this measure. It is thereby possible to visualize tumors with emphasis during the three dimensional display of the surface of the body interior by means of a previously applied substance that concentrates more strongly in the tumor tissue than in sound tissue and can be excited optically to fluoresce.

It can be provided in this case that only the regions of the surface of the body interior that are tissue-specific abnormal are inserted in the virtual model under fluorescence excitation.

In a further preferred refinement of the method, the at least one endoscopic image superposed with the aid of the virtual model on the surface of the body interior is optionally displayed in three dimensional or three dimensional fashion, the two dimensional display preferably being derived from the three dimensional display by means of a computer aided projection method. The Mercator projection, for example, is such a method.

In addition to the three dimensional display, the two dimensional display has the advantage of an improved clarity of the display, since the entire surface of the body interior can be displayed in one image in a plane.

In a further preferred refinement of the apparatus according to the invention, the position acquisition system for acquiring the position and orientation of the endoscope has an inertial sensor system fixed to the endoscope.

Starting from a reference point at which the endoscope is located at the beginning of the method, the Inertial sensor system is used to acquire all movement, that is to say all changes in position, as well as all changes in orientation of the endoscope by measuring acceleration, and the current position and orientation of the endoscope are determined therefrom. The use of an inertial sensor system for position acquisition of the endoscope has the advantage that such a system is self sufficient, that is to say manages without extracorporeal subsystems such as is the case, for example, in a position acquisition system having electromagnetic coils whose position and orientation are determined in an external magnetic field.

Further advantages and features emerge from the following description and the attached drawing.

It is self evident that the features named above and still to be explained below can be used not only in the respectively specified combination, but also in other combinations or on their own without departing from the scope of the present invention.

BRIEF DESCRIPTION OF THE DRAWINGS

Selected exemplary embodiments are described hereafter with reference to the attached drawings, in which.

DETAILED DESCRIPTION OF EXEMPLARY EMBODIMENTS

Figure 1:
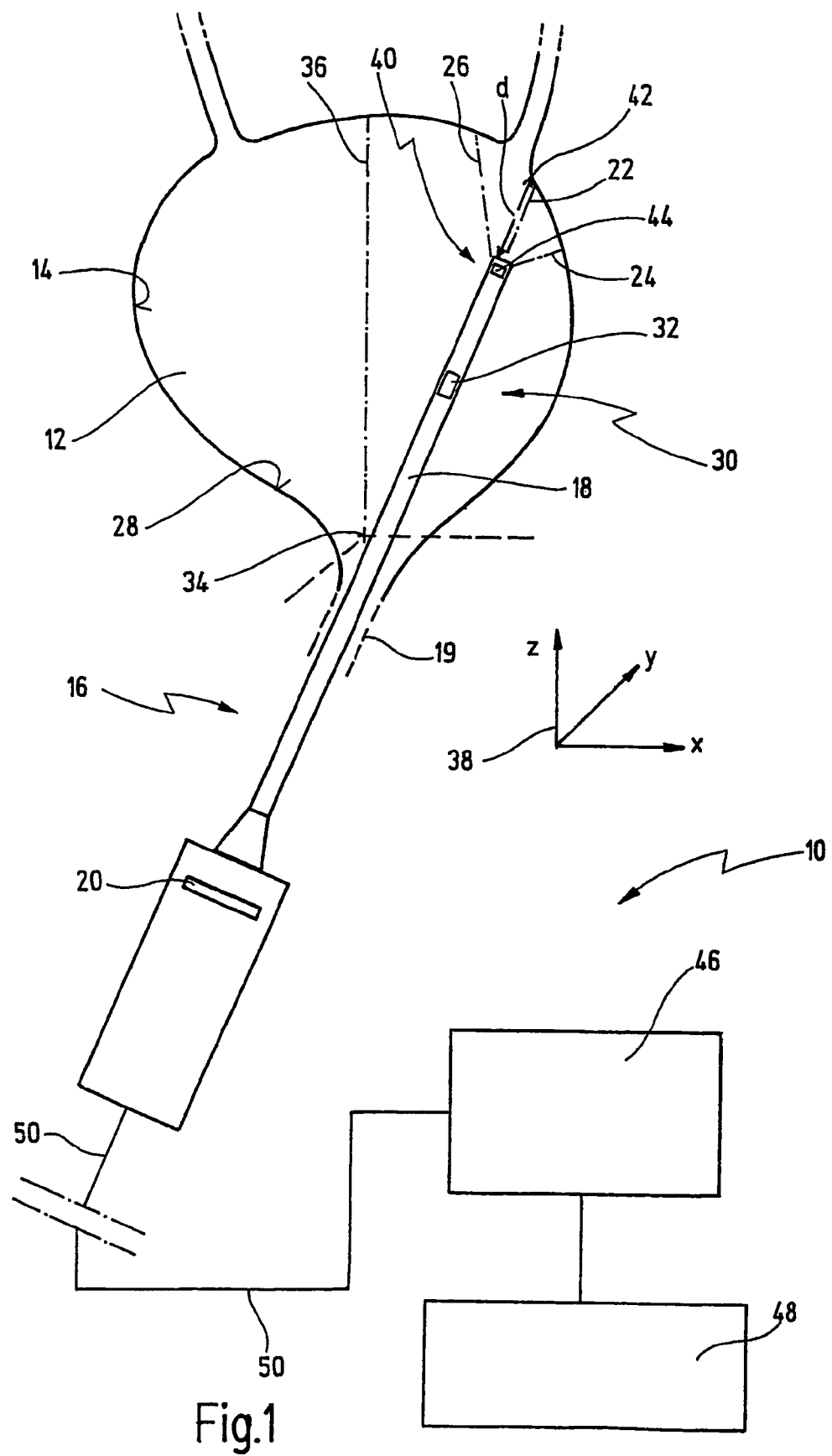
FIG. 1 shows an extremely diagrammatic illustration of an apparatus for generating at least one section of a virtual 3D model of a body interior.

FIG. 1 illustrates an apparatus, provided with the general reference symbol 10, for at least partially generating a 3D model of a body interior 12. In the exemplary embodiment shown, the body interior 12 is the bladder of a patient. More exactly, the apparatus 10 is used to acquire a surface 14 of the body interior 12 endoscopically in three dimensions. The apparatus 10 enables an endoscopic documentation of the preferably entire surface 14 of the body interior 12, and is yet to be described hereafter.

The apparatus 10 has an endoscope 16 with a shaft 18, which endoscope and shaft can be introduced into the body interior 12. In the present exemplary embodiment, in which the body interior 12 is the interior of a bladder, the shaft 18 is introduced into the bladder via the urethra 19.

The endoscope 16 can be a so called rigid endoscope, that is to say in this case the shaft 18 is rigid, or the endoscope 16 can be a flexible endoscope, the shaft 18 then being of flexible configuration. In the exemplary embodiment shown, the endoscope 16 is a rigid endoscope.

The endoscope 16 is preferably a video endoscope that is equipped with a camera 20 that, as illustrated in the present exemplary embodiment, is arranged in a proximal region of the endoscope 16, but can also be arranged in the distal region of the endoscope. In the case of the arrangement of the camera 20 in the proximal region, the endoscope 16 has an image transmission system in the shaft 18, for example in the form of a relay lens arrangement or an ordered optical fiber bundle.

The endoscope 16 is characterized by a viewing direction 22 and by an image field or field of view that is determined, in turn, by the numerical aperture of the objective of the endoscope 16. The angular aperture of the field of view is illustrated in FIG. 1 by boundary lines 24 and 26. The endoscopic image, acquired by the endoscope 16, of the surface 14 of the body interior 12 is substantially circular or, depending on the shape of the surface 14, in the shape of a conic section.

The apparatus 10 can have further endoscopes (not illustrated) that can be introduced alternately into the body interior 12 in exchange for the endoscope 16, these endoscopes then differing from one another through the direction of view 22. For example, the endoscope 16, whose direction of view 22 is 0° direction of view, can be exchanged for an endoscope having an 120° optic so as, for example, also to be able to acquire a rearwardly positioned surface area 28 by an endoscopic Image. However, this can also be achieved by virtue of the fact that instead of having one or more rigid endoscopes, the apparatus 10 has one flexible endoscope whose direction of view can be varied by deflecting the distal end of the shaft.

The apparatus 10 further has a position acquisition system 30 for acquiring the position and orientation of the endoscope 16. The position acquisition system 30 has an Inertial sensor system 32 that is arranged fixed in position on the endoscope 16, for example as illustrated in FIG. 1, in a distal region of the shaft 18 of the endoscope 16. The inertial sensor system 32 can be arranged on the outside of the shaft 18 or in the interior of the shaft 18.

The inertial sensor system 32 acquires the position and orientation of the endoscope 16 by virtue of the fact that it has sensors which detect the rotations and translations in space, the inertial sensor system 32 being capable of detecting all the six translational and rotational degrees of freedom of the endoscope 16. The opening of the urethra 19 into the bladder, for example, can be used in the present case as reference point 34 for acquiring the positions of the endoscope 16. As reference axis 36 for acquiring the orientation of the endoscope 16, it is possible for example, to use the central axis of the body interior 12, here of the bladder, and to use an axis fixed to the shaft for the rotational position of the endoscope about its longitudinal axis.

An appropriate reference coordinate system 38 is illustrated separately in FIG. 1.

The apparatus 10 further has a distance measurement system 40 for acquiring at least one distance, respectively dependent on the position and orientation of the endoscope 16, of the endoscope 16 relative to a point 42 on the surface 14 of the body interior 12. The distance measurement system 40 is a contactless distance measurement system that is arranged on the endoscope 16 and has, for example, a laser light source 44 that directs at least one laser beam onto the surface 14 of the body interior 12, preferably doing so In the direction of the direction of view 32, that is to say the distance measurement is preferably performed in the middle of the image cone of the endoscope 16 that is bounded by the lines 24 and 26. The abovementioned laser light beam is used to acquire a distance d for example on the basis of a triangulation or by measuring the transit time of the laser light beam from the laser light source 44 to the point 42 and back again to the laser light source, where an appropriate sensor is fitted.

Other preferred possibilities of configuring the distance measurement system 40 can consist in using the laser light source 44 to project a pattern onto the surface 14 of the body interior 12, for example a striped, grid or punctiform pattern. However, instead of a laser light source 44, it is also possible to arrange an ultrasound source on the endoscope 16, the distance measurement system 40 then acquiring the distance d by means of the ultrasound emitted by the ultrasound source by measuring the transit time of the ultrasound in a fashion similar to the measurement of transit time by means of a laser beam.

The distance measurement system according to one of the previously mentioned types can, in particular, be modified such that it can acquire the distance of the endoscope 16 from the surface 14 simultaneously at a number of points within the image field cone.

The apparatus 10 further has a data processing system 46 and a monitor 48.

Running together in the data processing system 46 via a signal line 50, for example, are the signals or data of the position acquisition system 30, the distance measurement system 40 and the camera 20, which receives an endoscopic image in the associated position and orientation of the endoscope 16 and at the associated distance d.

The data processing system 46 is designed such that it can use a plurality of points of the surface 14 of the body interior 12 that have been acquired in three dimension from different positions and orientations of the endoscope 16 by the distance measurement system 40 to generate at least partially a virtual model of the surface 14 and in so doing to project the optically acquired endoscopic images onto the model thus generated such that the three dimensionally acquired surface 14 of the body interior 12 is displayed on the monitor 48 with endoscopic image information. The preferably entire surface 14 acquired endoscopically in three dimensions can then be stored for documentation in the data processing system 46 in order to reuse this stored information for later examinations of the body interior 12, for example in order to be able to assess the cause of an illness or a course of therapy with regard to its development.

In the case of the method for the at least partial 3D modelling of the body interior 12, more precisely its surface 14, the virtual 3D model of the surface 14 of the body interior 12 is thus correspondingly obtained by acquiring a plurality of endoscopic images from different positions of the endoscope 16, the position and orientation of the endoscope 16 being acquired relative to each endoscopic image by means of the position acquisition system 30 as well.

In addition, the distance measurement system 40 is used to acquire the distance d from the point 42 on the surface 14 of the body interior 12 in relation to each endoscopic image and acquired position and orientation of the endoscope 16.

Figure 2:
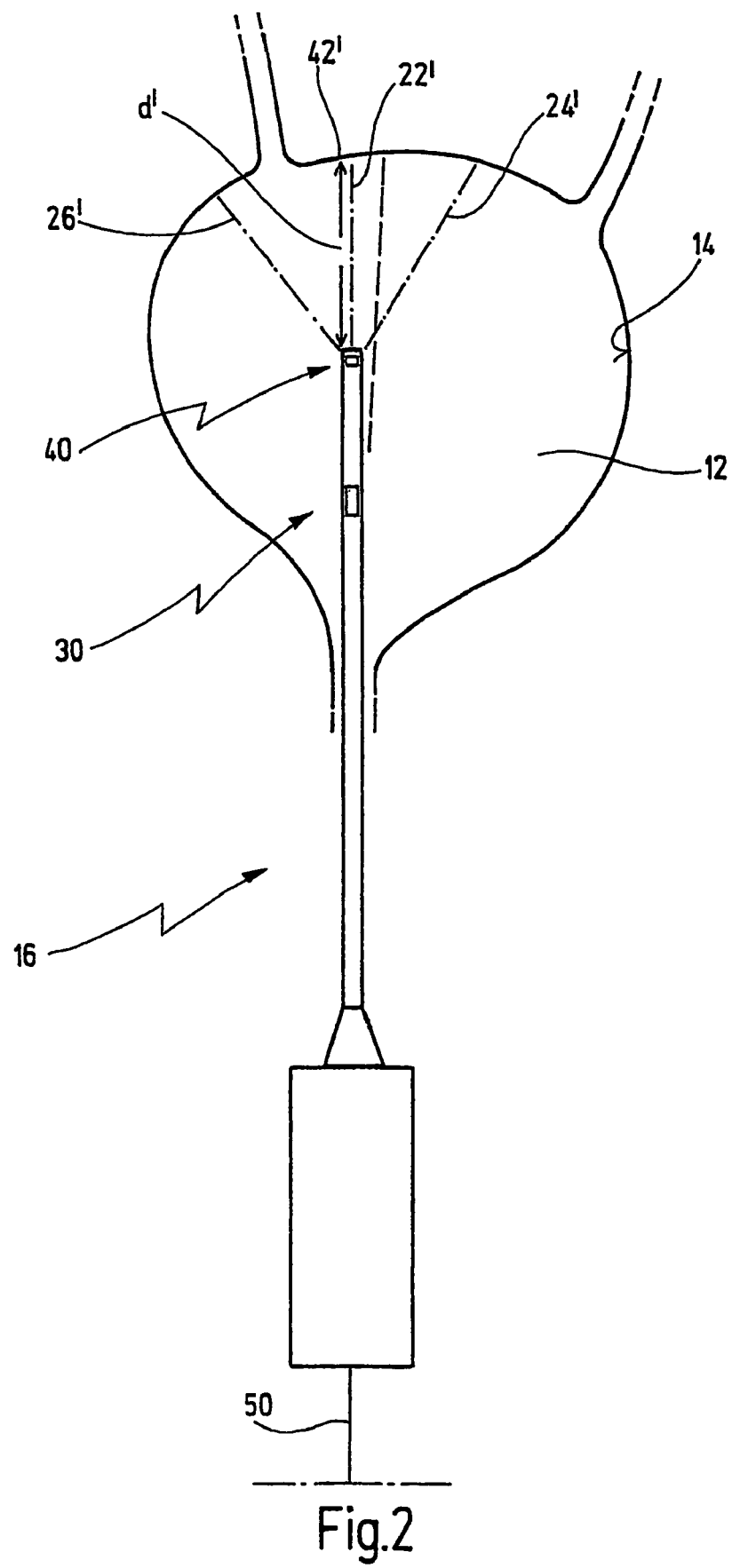
FIG. 2 shows the apparatus in FIG. 1 with the omission of parts in an operating state modified by comparison with FIG. 1.

For the purposes of illustration, the endoscope 16 is illustrated in FIG. 2 In the body interior 12 in a position and orientation modified by comparison with FIG. 1, this orientation and position of the endoscope 16 being acquired, in turn, by means of the position acquisition system 30, and a distance d' from a point 42' on the surface 14 of the body interior 12 simultaneously being acquired, again in the direction of the direction of view 22, by means of the distance measurement system 40. The associated endoscopic image of the surface area lying inside the boundary 24, 26 of the field of view is likewise acquired.

The above named data, specifically the various positions and orientations of the endoscope and the associated endoscopic images and corresponding distances d of the endoscope 16 from the surface 14 of the body interior 12 are then used to generate the three dimensional virtual model of the surface 14 of the body interior 12, and the respectively acquired endoscopic image is then projected, with the aid of the acquired position and orientation of the endoscope 16, which is acquired with the aid of the position acquisition system 30, onto the corresponding surface area of the virtual model of the body interior 12. Any possibly overlapping endoscopic images are superposed on one another in the data processing system 46 in the correct position, for example, or are tailored such that there is no longer any overlap.

The distance measurement by means of the distance measurement system 40 Is triggered as automatically as possible in this case, for example at intervals of a few milliseconds. The acquisition of position by means of the position acquisition system 30 is also triggered automatically, preferably in a fashion synchronized with the distance measurement.

Figure 3:
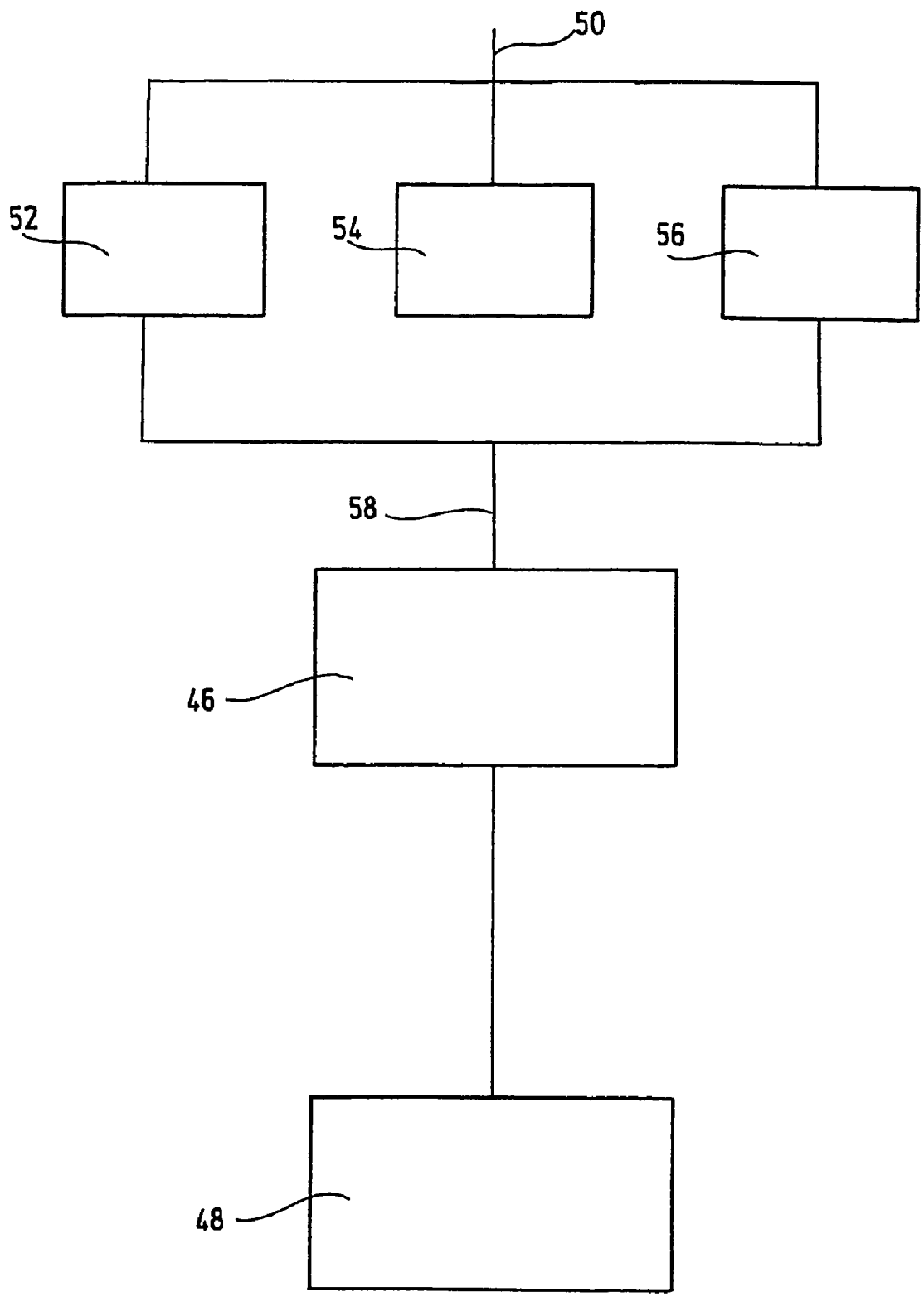
FIG. 3 shows a block diagram of the method for generating at least one section of a virtual 3D model of the body interior.

The method is outlined roughly in a block diagram in FIG. 3; 52 denotes the individual position acquisition of the endoscope 16, 54 the individual distance measurement of the distance d of the endoscope 16 from the surface 14 of the body interior 12, and 56 the endoscopic image 56 respectively acquired during the position acquisition 52 and distance measurement 54. This information is then fed via a signal line 58 to the data processing system 46 in which this information is processed such that the abovementioned virtual three dimensional model of the surface 14 of the body interior 12 is generated, and the endoscopic image 56 that originates from an area of the surface 14 is projected onto the corresponding surface area or the corresponding section of the model of the surface 14.

The three dimensionally reconstructed surface 14 of the body interior 12 is then displayed on the monitor 48 together with the endoscopic image information projected thereon.

It is, furthermore, preferably provided to mark visually on the virtual model of the surface 14 of the body interior 12 thus generated those surface areas or sections of which an endoscopic image has already been acquired. The doctor is able in this way to establish which areas of the surface 14 he has already examined, and which he has not.

The marking, for example marking in color or black and white, of the surface areas 14 of the body interior 12 for which an endoscopic image has already been acquired, can be performed by acquiring the hold time of the viewing of these surface areas, by using a different light intensity, and/or by using a signal that is generated during viewing of a specific surface area. The marking of the surface areas with the aid of the hold time of the viewing increases the reliability in the examination of the body interior 12, because it can be assessed from the hold time whether the corresponding surface area has actually been thoroughly inspected by the doctor, or whether the endoscope 16 has passed over the surface area only in a cursory, even only in an accidental fashion.

Figure 4:
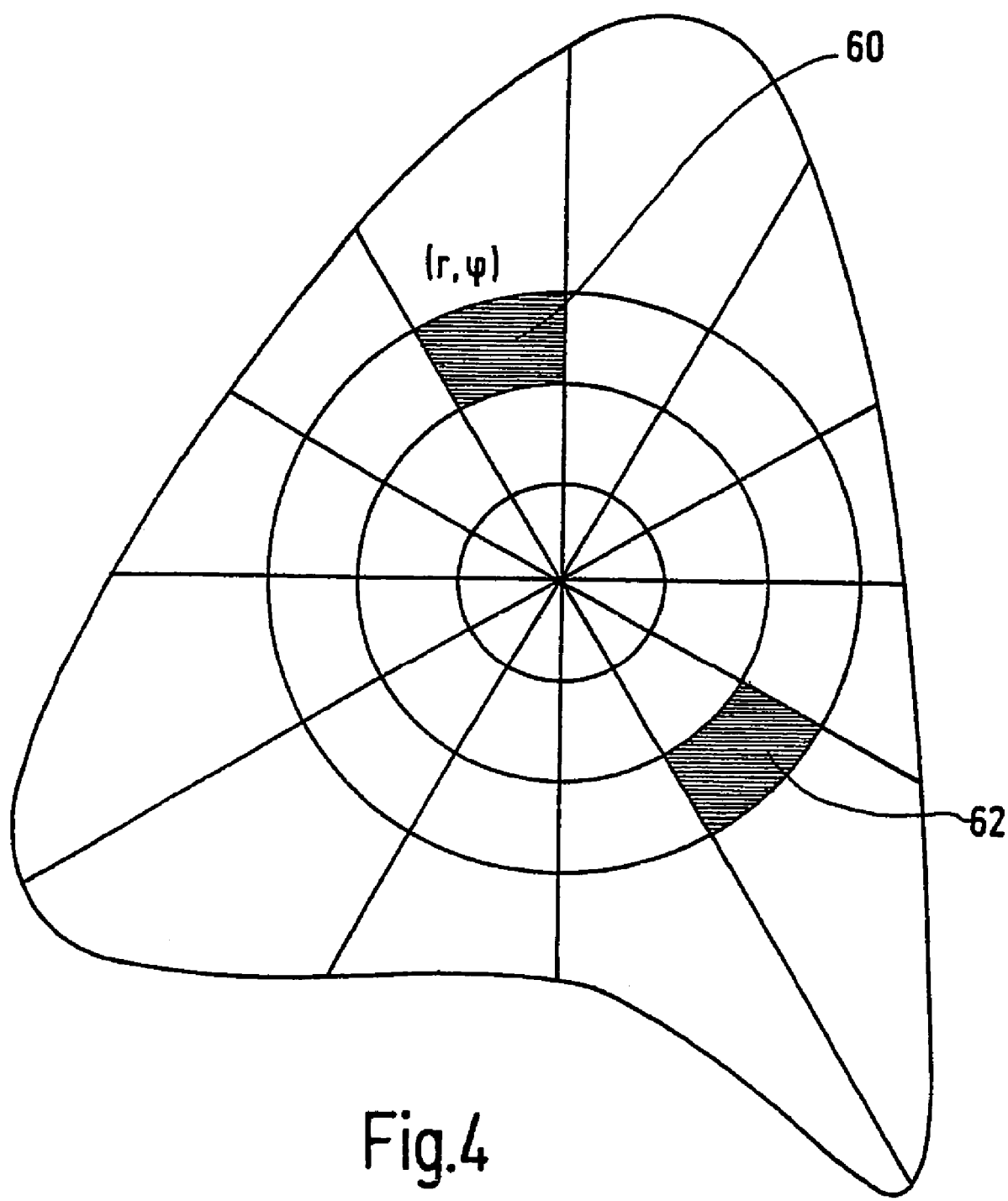
FIG. 4 shows, projected into a plane, a display that has been obtained from a three dimensional model of the surface of the body interior.

The image on the monitor 48 is illustrated by the example in FIG. 4. As already mentioned, the three dimensionally reconstructed surface 14 of the body interior 12 can be displayed in three dimensions on the monitor 48, that is to say perspectively, or, as illustrated in FIG. 4, the three dimensionally reconstructed surface 14 of the body interior 12 can be projected into a plane (for example Mercator projection) and this can then be illustrated two dimensionally on the display screen.

Also illustrated by way of example in FIG. 4 are two marked surface areas 60 and 62 for which an endoscopic image has already been acquired.

Furthermore, it can preferably be provided that the virtual model, together with endoscopic images of the surface 14 of the body interior 12 projected thereon, is additionally superposed in the data processing system 46 with an image of the body interior 12 obtained by an imaging method having a depth effect, for example computed tomography, magnetic resonance, ultrasound, in order, in addition to the optical surface information relating to the body interior 12, to obtain depth information, for example data on the depth of a malign region of the tissue below the surface 14 of the body interior 12, or relating to neighboring tissue and organs. In this case, the data processing system 46 can be designed such that it generates a further virtual 3D model of the body interior 12 from information obtained by an imaging method having a depth effect. The data processing system 46 is then preferably designed in such a way that the monitor 48 provides a viewing mode in which, starting from the endoscopic image of the surface, it is possible to continue to view in the viewing direction of the endoscope 16 the positionally correct 3D information, which is obtained from the imaging method having a depth effect. In this way a so called look ahead function is realized.

Furthermore, it can likewise preferably be provided to obtain the previously mentioned virtual model of the surface 14 of the body interior 12 at least partially under fluorescence excitation as is the case with so called photodynamic diagnosis. In addition to the three dimensional reconstruction and endoscopic visual display of the surface 14 of the body interior 12, it is thus possible for tumors to be more plainly visualized on the basis of different fluorescence signals from different areas of the surface 14. When the virtual 3D model of the surface 14 of the body interior 12 is derived from endoscopic images that can be at least partially obtained under fluorescence excitation, it is preferably possible to provide that only the regions under fluorescence excitation that are tissue-specific abnormal, that is to say pathological, are inserted in the virtual model.

What is claimed is:

1. A method for generating at least one section of a virtual 3D model of a body interior from data that are provided by at least one endoscope introduced into said body interior, wherein said data comprise at least one position and orientation of said endoscope, comprising the steps of: assigning said at least one position and orientation of said endoscope at least one distance between said endoscope and at least one point on a surface of said body interior, assigning said at least one position and orientation of said endoscope at least one endoscopic image of said surface of said body interior in a region of said at least one point on said surface of said body interior, generating said at least one section of said 3D model in superposition with said at least one endoscopic image by using said data relating to a number of different positions and orientations of said endoscope.

2. The method of claim 1, wherein surface areas of said surface of said body interior of which an endoscopic image has already been acquired are visually marked on said virtual 3D model of said body interior.

3. The method of claim 2, wherein said marking of said surface areas of said body interior in relation to which an endoscopic image has already been acquired is performed with the aid of an acquisition of a hold time for viewing said surface areas.

4. The method of claim 2, wherein said marking of said surface areas of said body interior in relation to which an endoscopic image has already been acquired is performed with the aid of a different light intensity.

5. The method of claim 2, wherein said marking of said surface areas of said body interior in relation to which an endoscopic image has already been acquired is performed with the aid of a signal that is generated during viewing of a specific surface area.

6. The method of claim 1, wherein said at least one distance between said endoscope and said at least one point on said surface of said body interior is acquired by at least one laser beam emitted by said endoscope.

7. The method of claim 6, wherein said at least one distance between said endoscope and said at least one point on said surface of said body interior is acquired by said at least one laser beam stereoscopically on the basis of a triangulation.

8. The method of claim 6, wherein said at least one distance between said endoscope and said at least one point on said surface of said body interior is acquired by said at least one laser beam by measuring a transit time of said laser beam.

9. The method of claim 1, wherein said at least one distance between said endoscope and said at least one point on said surface of said body interior is acquired by a pattern projected by said endoscope onto said surface of said body interior.

10. The method of claim 1, wherein said at least one distance between said endoscope and said at least one point on said surface of said body interior is acquired by ultrasound emitted by said endoscope by measuring a transit time of said ultrasound.

11. The method of claim 1, wherein said distance measurement is carried out in time intervals that are shorter than 1 second.

12. The method of claim 11, wherein said distance measurement is carried out in time intervals in a range of lower than 1 millisecond.

13. The method of claim 1, wherein said at least one section of said virtual 3D model of said body interior is superposed with said at least one endoscopic image with an image of said body interior obtained by an imaging method having a depth effect.

14. The method of claim 1, wherein said virtual 3D model of said surface of said body interior is derived from endoscopic images that are firstly obtained partially under fluorescent excitation.

15. The method of claim 14, wherein only those surface areas under fluorescence excitation that are tissue-specific abnormal are inserted in said virtual 3D model.

16. The method of claim 1, wherein said virtual 3D model Is converted from a 3D display into a 2D display.

17. An apparatus for generating at least one section of a 3D model of a body interior, comprising at least one endoscope for acquiring at least one endoscopic image of at least one surface area of a surface of said body interior, a position acquisition system for acquiring a position and orientation of said endoscope, a distance measurement system for acquiring at least one distance of said endoscope in relation to at least one point of said surface of said body interior as a function of said position and orientation of said endoscope, and a data processing system using a plurality of points, acquired from different positions and orientations of said endoscope by said distance measurement system, on said surface of said body interior to generate said at least one section of said 3D model of said surface of said body interior and projecting said at least one endoscopic image onto said 3D model.

18. The apparatus of claim 17, wherein said processing system marks visually on said 3D model of said body interior those surface areas for which an endoscopic image has already been acquired.

19. The apparatus of claim 17, wherein said data processing system derives a further virtual 3D model of said body interior from an image of said body interior obtained by an imaging method having a depth effect.

20. The apparatus of claim 19, wherein said data processing system superposes said 3D model in the correct position on said further virtual 3D model.

21. The apparatus of claim 19, wherein said data processing system enables a viewing mode in which, starting from said endoscopic image of said surface of said body interior, it is possible to continue to view in a viewing direction of said endoscope the virtual 3D model obtained from said imaging method having a depth effect.

22. The apparatus of claim 17, wherein said position acquisition system has an inertial sensor system fixed to said endoscope.

23. The apparatus of claim 17, wherein said distance measurement system is a contactless distance measurement system.

24. The apparatus of claim 17, wherein said distance measurement system is arranged on said endoscope.

25. The apparatus of claim 17, wherein said distance measurement system is integrated in said endoscope.

* * * * *